United States Patent [19]

Kovacs et al.

[11] Patent Number: 5,211,663
[45] Date of Patent: May 18, 1993

[54] PASSIVATION METHODS FOR METALLIC MEDICAL IMPLANTS

[75] Inventors: Paul Kovacs, Memphis; James A. Davidson, Germantown, both of Tenn.

[73] Assignee: Smith & Nephew Richards, Inc., Memphis, Tenn.

[21] Appl. No.: 719,805

[22] Filed: Jun. 24, 1991

[51] Int. Cl.$^5$ ............... A61F 2/28; A61F 2/30; A61F 2/02; A61K 1/02
[52] U.S. Cl. ............................ 623/16; 623/18; 623/11; 427/2
[58] Field of Search ............... 623/16, 11, 18; 427/2

[56] References Cited

U.S. PATENT DOCUMENTS

| | | |
|---|---|---|
| 3,643,658 | 2/1972 | Steinemenan . |
| 3,663,379 | 5/1972 | Kendall ............................. 204/56 |
| 3,873,512 | 3/1975 | Latanision ..................... 204/129.46 |
| 4,336,617 | 6/1982 | Shikita et al. . |
| 4,441,968 | 4/1984 | Emmer et al. .................... 204/35 N |
| 4,444,601 | 4/1984 | Greene ............................. 148/31.5 |
| 4,495,664 | 1/1985 | Blanquaert . |
| 4,717,456 | 1/1988 | Chessin et al. ....................... 204/34 |
| 4,765,870 | 8/1988 | Emmer et al. .................... 204/129.1 |
| 4,846,837 | 7/1989 | Kurze et al. ............................ 623/16 |

FOREIGN PATENT DOCUMENTS 0222717 5/1987 European Pat. Off. .
0447744 9/1991 European Pat. Off. ............. 623/18

OTHER PUBLICATIONS

Norio Sato, "Toward a More Fundamental Understanding of Corrosion Processes", *Corrosion*, 45, 354–368, May 1989.
Aragon and Hulbert, "Corrosion of Ti-GAL-4V in Simulated Body Fluids and Bovine Plasma", *J. Biomed. Mat. Res.*, 6, 155–164, 1972.
Grant & Hackh's Chemical Dictionary, 5th Edition, p. 217.
"Corrosion-resistant alloys in chlorine solutions: materials for surgical implants", T. P. Hoar and D. C. Mears, Ref. Proc. Royal Soc. (London), SCR.A294 (1439), 1966, pp. 486–510.
Revie, R., et al., *Corrosion Science*, 9: 763–770, 1969.
Metals Handbook Ninth Ed., 13, 552.

Primary Examiner—David Isabella
Assistant Examiner—Dinh X. Nguyen
Attorney, Agent, or Firm—Shaukat A. Karjeker

[57] ABSTRACT

Passivated implants and passivation methods that provide superior corrosion resistance and surface performance characteristics as compared to conventional nitric acid passivation are disclosed. The method uses either the spontaneous or galvanic passivation of metallic prosthetic implants in aqueous alkali salt solutions containing non-aggressive oxyanions to produce a thin and uniform passive coating on the metal implant, thereby rendering the implant more stable in the biological environment.

14 Claims, 6 Drawing Sheets

PASSIVATION METHODS FOR METALLIC MEDICAL IMPLANTS

BACKGROUND OF THE INVENTION

1. Field of the Invention

This invention relates to the passivation of metallic medical implants and passivated metallic medical implants produced by these methods; and, in particular, to passivation methods that result in superior corrosion resistance and performance characteristics, as compared to conventional nitric acid passivation.

2. Background

The majority of metals are thermodynamically unstable in aqueous solutions and tend to oxidize easily in the presence of hydrogen ions, oxygen, and water because the free energy change during the formation of oxides has a significantly negative value. Nevertheless, certain metals such as iron, aluminum, chromium, nickel, titanium, zirconium, niobium, and tantalum as well as their alloys react very slowly with the above substances, due to the presence of a protective surface film that markedly reduces the corrosion rate. Passive surface films are those thin films (up to roughly 10 nanometers, depending on the material) which spontaneously form to maintain surface passivity. For example, stainless steel is stainless because of the thin protective chromium oxide/hydroxide passive film which can form in air.

The occurrence of passivity makes it possible to use metals in chemically aggressive media, even in the physiological environment which is particularly hostile to metals. Virtually all metallic medical implants (such as, for instance, stainless steels, Co—Cr—Mo alloy, titanium, and Ti—6Al—4V alloy, tantalum, etc.) must exhibit a minimum level of self-maintained passivity in the human body. That is, the passive oxide/hydroxide film on the metallic implant must not only withstand chemical attack by damaging species, like chloride ions which are abundantly available in the body fluids, but it also must effectively redevelop if mechanically removed, i.e. it must spontaneously repassivate.

Mechanical disruption of the passive film may occur from abrading against adjacent bone due to motion of the implant, or from articulation against counter bearing surfaces, such as ultra high molecular weight polyethylene. During repassivation, significant amounts of dissolved metal ions can be produced, depending on the degree of surface destruction and on the quality of the passive film on the undisturbed surface portion of the implant. The long-term consequences of metal ion release into the body environment are not well understood; however, it is generally accepted that such release should be minimized. Thus, the effectiveness of a passive surface film is an important aspect of implant biocompatibility.

The nature of the passive film primarily depends on the metal and the conditions under which it develops. The protection provided by this surface layer in a specific environment is mainly determined by the stability of the passive film in the specific environment.

The unique feature of biomedical applications is that the implant metal or alloy must not only be safeguarded, but its effects on the physiological environment must also be considered. Commonly used implant metals include low carbon austenitic stainless steel (AISI types 316L, 316, 303, and 304); cobalt-chromium alloy (ASTM F-75, F-90, F-799); and titanium and titanium alloys such as Ti—6Al—4-V alloy (ASTM F-136), PROTASUL 100 (Ti—6Al—7Nb).

For adequate biocompatibility, the effectiveness of the passive film on a metallic implant is extremely important because adverse action between the implant material and the body fluids has to be prevented. It is desirable that the implant should not corrode and, if it does corrode, then the biological environment should not be adversely affected by the corrosion products. This latter requirement highlights the need for a unique, entirely different approach to the use of metal and coated metals in biomedical systems.

In addition to conventional corrosion considerations, the release of corrosion products into the physiological environment should also be minimized based on a biological scale. Creating overly positive initial corrosion potentials by enforced, drastic passivation should also be avoided in order to eliminate the formation of metal ions (e.g., $Cr^{6+}$ ions) with undesirable biological effects, or not to induce processes such as blood clotting on the implant surface, which may further result in thrombosis and inadequate blood compatibility. An effective passivation method, therefore, must produce a protective layer in the metallic implant which is similar to the one that develops spontaneously in body fluids, and which undergoes the least structural and compositional changes after implantation (hence, minimizing metal ion release into the body).

The passivation method currently used for metallic biomedical implants is essentially routine passivation by nitric acid, according to ASTM F-86 "Standard Practice for Surface Preparation and Marking of Metallic Surgical Implants." This practice provides a description of final surface treatment with nitric acid, using the following procedure: "Immerse in 20 to 40 volume % nitric acid (specific gravity 1.1197 to 1.2527) at room temperature for a minimum of 30 min. For an accelerated process, this acid solution, heated from 120° to 140° F. (49° to 60° C.), may be used for a minimum of 20 min.—Employ thorough acid neutralizing and water rinsing process and a thorough drying process."

The initial oxide/hydroxide layer that develops spontaneously on the metallic implant prior to the final passivation may considerably affect the quality of the passive film. That is, if a metal is covered by a non-coherent surface layer that has formed during processing and cleaning procedures, exposure to a powerful oxidizing agent like nitric acid can easily result in a thick but considerably rough passive layer, depending on how uniform the previously developed spontaneous surface layer was.

In the late 1960's and early 1970's, efforts were made to evaluate the effectiveness of the nitric acid passivation performed according to ASTM F-86. Revie and Green (Corrosion Science, vol. 9 p. 763-770 (1969) contend that prepassivation in oxygenated NaCl solution markedly improves the corrosion resistance of implant materials (except for titanium). The authors recommended this passivation method in preference to any form of $HNO_3$ treatment for types 304 and 316 stainless steels and Vitallium (cobalt) alloy. They also stated that routine storage of all metallic implants in oxygenated isotonic NaCl could easily be adopted because of its ease of handling and its availability in all hospitals. Similar conclusions were drawn by Aragon and Hulbert for Ti—6Al—4V alloy. J. Biomed. Mater. Res., vol. 6 p. 155-164 (1972). These researchers suggested that preparation techniques for Ti and Ti-alloys, other than the ASTM recommended practice F-86(68), should be explored and storage of the prosthesis in isotonic saline solution should give good results.

The saline passivation of metallic surfaces has never been introduced as a routine industrial passivation procedure. While the Revie and Green results indicate that nitric acid passivation does not result in optimum performance characteristics for biomedical applications, saline passivation does not produce the best protective layer either.

In Sato, "Toward a More Fundamental Understanding of Corrosion Processes," 45 *Corrosion* 354 (1989), the author discloses that, in the presence of a neutral chloride solution, an anion-selective precipitate film is formed on the surface of corroding metal due to selective mass transport in anodic corrosion processes. When the anodic metal corrosion proceeds under such a precipitate film, the internal occluded solution (i.e. the solution layer between the metal and the passivated layer) will become enriched in both metal ions and chloride ions, because the anodic current throughout the anion-selective precipitate film is carried mainly by the chloride ion migrating from the external bulk solution to the occluded solution. Both the accumulation of metal chloride, leading to acidification, and the continuous electro-osmotic flow of water molecules into the occluded solution, will provide conditions favorable for localized corrosion to take place under an anion-selective corrosion precipitate. Hence, a less uniform passive film is likely to develop in the presence of aggressive chloride ions.

Sato also contends that the presence of cation-selective corrosion precipitates on the surface of corroding metals is favorable. In this instance, chloride ions are prevented from migrating into the occluded solution. Instead, the anodic corrosion current through the precipitate film is carried by predominantly mobile cations, such as hydrogen ions, which migrate outward leaving dissolved metal ions in the occluded solution. This eventually results in the formation of metal hydroxides at a rate controlled by the inward diffusion of water through the corrosion precipitate film. Under these conditions, there is no accelerated corrosion propagation and corrosion will be retarded. Most of the non-aggressive oxyanions in common use, such as sulfate, borate, chromate, molybdenate, and tungstate, are capable of converting anion-selective hydrated metal oxides to cation-selective phases by their adsorption or incorporation into the phases.

There exists a need for metallic implants surface passivated with a tightly adherent coating that exhibits improved long term corrosion resistance in the body. Further, the passivated surface should be easily formed by conventional manufacturing processes and be resistant to those conventional sterilization techniques that implants undergo before surgical implantation.

SUMMARY OF THE INVENTION

The invention provides passivated metal implants with superior in vivo corrosion resistance and methods of passivating metal implant surfaces for corrosion resistance in the body. The invention implants are covered with a thin, uniform tightly adherent oxide/hydroxide coating (i.e. coating of oxide, coating of hydroxide or coating of a mixture of oxide and hydroxide) that is resistant to corrosion in the body. In the invention methods, the metallic implant surfaces are either spontaneously or galvanically passivated in aqueous water soluble salt solutions, preferably alkaline metal salt solutions, containing non-aggressive oxyanions such as sulfate, phosphate, di-hydrogen phosphate, mono-hydrogen phosphate, borate, and the like. Galvanic passivation in these electrolytic solutions may be achieved by galvanic coupling of the metal or alloy implant with an electrochemically more noble material, such as carbon. Such passivation methods, utilizing non-aggressive oxyanions, provide a thin and uniform passivated surface on the metal implant, thereby rendering the implant more stable in the biological environment, and therefore more biocompatible.

In both the spontaneous and galvanic surface passivation methods, aggressive oxyanions and chloride ions are excluded from the passivating solutions resulting in a more uniform barrier film which is less prone to localized breakdown processes when placed into the biological environment. Additionally, since the nature of the inventive passivating solutions is more similar to that of body fluids, than nitric acid, the protective ability of the invention passive film, when exposed to the body fluids, undergoes much less alteration. The inventive methods also reduce the disadvantageous effects of initial surface conditions on the effectiveness of passivation. This is largely due to the absence of aggressive species that may further enhance the non-uniform character of the initial surface film.

In the galvanic method there is galvanic coupling of the metal or alloy implant with, for instance, carbon. Without being bound, it is theorized that the macroscopic separation of anodic and cathodic processes may give rise to a lower local pH at the metal surface and, this may assist in the removal of undesirable corrosion products from the passive film. Since the breakdown potential in the passivating solution is much more positive than the potential at which anodic dissolution takes place, no specific restriction on the metal/carbon surface area ratio is necessary.

The invention provides relatively inexpensive methods of treating metallic implants to produce the invention coated implants that offer significant advantages in terms of corrosion resistance and that minimize the production of corrosion by-products in the body.

DETAILED DESCRIPTION OF THE PREFERRED EMBODIMENTS

Figure 1A:
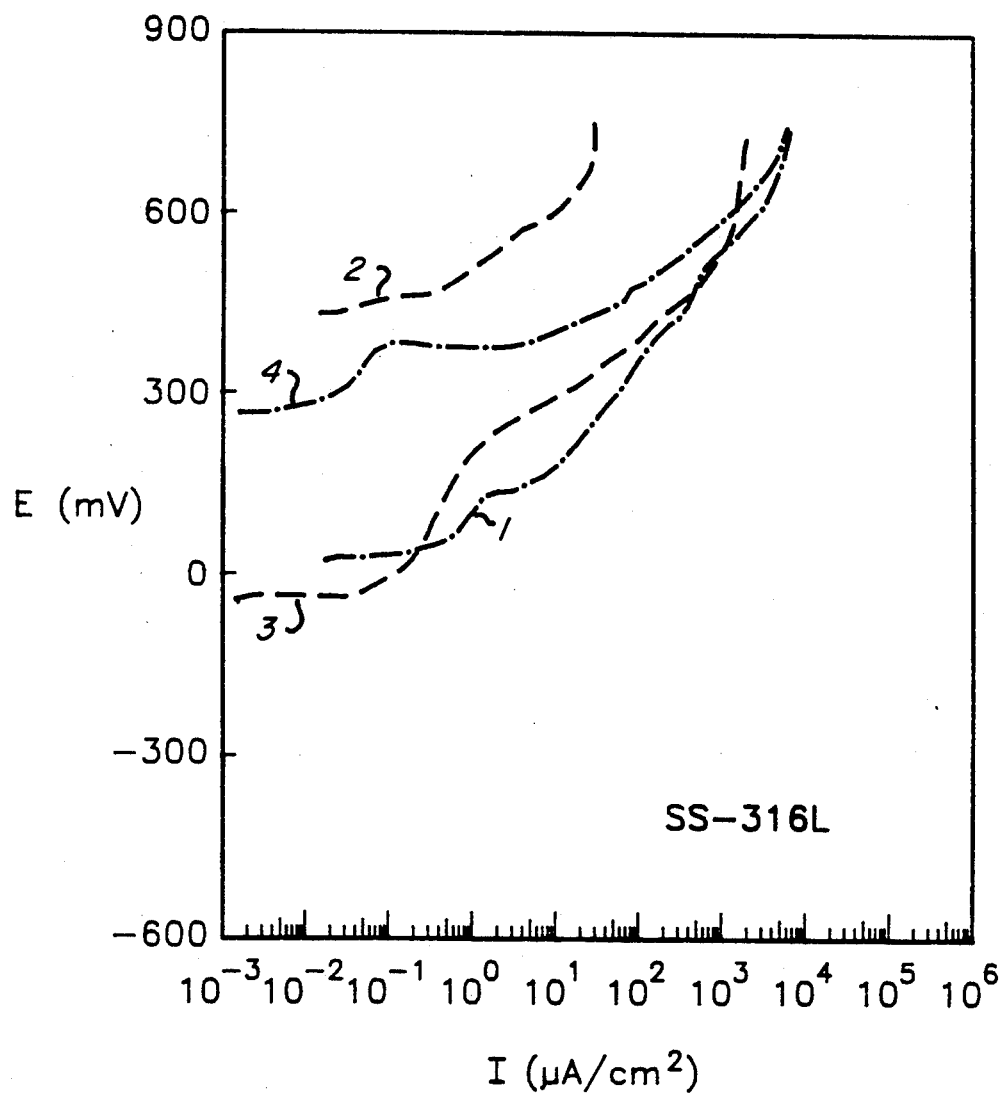
FIGS. 1a and 1b show the effect of initial and passivating conditions on two different samples of 316L stainless steel coupons.

The invention surface passivation methods are generally useful for passivating the surface of metallic implants. For example, the inventive surface passivation methods may appropriately be used for treating those metals and their alloys typically used as implant materials. These include, but are not limited to, stainless steels such as, for example, low carbon austenitic stainless steels such as AISI types 316, 316L, 303 and 304, cobalt-chromium alloys, cobalt-chromium-molybdenum alloys, and the like. Further, the method may be used to passivate the surface of implants fabricated from more exotic metals and their alloys, such as for instance, the Group 4 and 5 metals including zirconium, titanium, tantalum, and niobium.

As used in the specification and claims, "non-aggressive oxyanions" refer to chemically stable oxyanions whose presence promotes the formation of a uniform passive layer on the implant surface but does not chemically react with the implant surface. Further, "spontaneous passivation" refers to passivation without the macroscopic separation of the anodic and cathodic processes. Also, "galvanic passivation" refers to passivation with the macroscopic separation of the anodic and cathodic processes, but without the need for an outer current source. The term "thin" as applied to the passive oxide/hydroxide coatings refers to coatings of thickness from about 1 to about 20 nm, preferably from about 2 to about 3 nm.

Prior to passivation, the metallic implant surface should be prepared by the methods that are known in the prior art and that are prescribed for use with nitric acid passivation, but without the use of nitric acid. The implant should be wiped clean of any large debris and then cleaned to remove grease, coolant, or other shop debris. Optimum passivation results are obtained when the implant surface is first thoroughly cleaned (i.e. as clean as the implant would need to be for plating). Typical cleaning procedures are known to those skilled in the art, and include solvent cleaning (the solvent containing a degreaser), followed by an alkaline soak cleaning, and thorough water rinsing. In order to clean the implant, the implant may be immersed in the cleaning solution, swabbed with the cleaning solution, or the solution may be applied to the implant by pressure spraying.

An aqueous passivation solution is then prepared from the salts of water soluable metals, preferably alkali metals, with non-aggressive oxyanions. The non-aggressive oxyanion may be a sulfate, phosphate, monohydrogen phosphate, di-hydrogen phosphate, borate, and the like. The salt concentration of these passivation solutions may vary within a wide range, with the preferred concentration range being from about 0.05 equivalents per liter to about 0.25 equivalents per liter. The preparation of such solutions is well known to those of ordinary skill in chemistry and does not require any special skills or precautions, which are often necessary in the preparation of nitric acid passivation solutions.

The natural pH value of the solutions as set by the dissolution of the particular salts is preferred. However, the pH may also be adjusted by the corresponding acid, if desirable. Furthermore, the passivation solution may be oxygenated, e.g. by bubbling with purified air or oxygen, to improve the passivation processes.

After the passivating solution is prepared, the metallic implant is immersed in the solution, which is then preferably heated to a temperature is 20° C. to about 50° C. The preferred temperature is 37° C. (human body temperature). While temperatures greater than 50° C. can be employed, the greater the temperature, the faster is the passivation rate, resulting in a less uniform passive layer.

Depending upon the initial surface activity, spontaneous passivation may require that the metallic implant remain in the solution from about 2 hours to about 36 hours, depending upon the solution temperature. The preferred time during which the implant typically remains in the passivating solution, in order for spontaneous passivation to occur, is about 24 hours when the temperature is about 35°–40° C.

During the passivation process, a thin oxide/hydroxide film spontaneously forms on the metallic surface of the implant. The maximum film thickness that results is about 10 nm; however, the usual resulting thickness is from about 1 to about 8 nm, with the preferred passivating film layer thickness being 2–3 nm. The thinner film surface is preferred because it is usually more uniform and therefore provides better protection for the alloy surface. After a time sufficient to form the oxide/hydroxide film, the metallic implant is removed from the passivating solution, water rinsed, and dried.

In an alternative embodiment, the galvanic coupling of the metal or alloy implant with electrochemically more noble materials, such as carbon, is carried out in the previously described passivation solutions, using, for example, carbon racks. After the passivation solution is prepared, a mechanically coupled graphite rod and the metallic implant are both immersed in the electrolytic solution and heated to the same temperatures as specified for spontaneous passivation. The mechanical contact of this system establishes a natural galvanic couple with the resultant separation of the anode and cathode processes.

The effect of various initial and passivating conditions are illustrated in FIGS. 1–3, for two samples for each material (SS-316L, Co—Cr—Mo, and Ti—6Al—4V). The anodic polarization curves, one day after passivation, were determined potentiodynamically in lactated Ringer's solution open to air. Such a determination was obtained by applying varying potential differences (in millivolts) and measuring the reulting currents in microamps. In performing these tests, we used an AG & G Princeton Applied Research Model 173 Potentiostat and SoftCorr Model 332 Software. The resultant current density reading (x-axis, microamps $cm^2$) was then recorded and plotted against the particular applied potential difference versus a saturated calomel reference electrode (y-axis, millivolts) to obtain the polarization curve. This curve was then extrapolated to determine the passive corrosion current density (icorr). The icorr for the implant passivated by the example method (i.e. "icorr, example pass".) was then compared to the icorr for nitric acid passivation (i.e. icorr, HNO3 pass.) in the form of a ratio:

$$\frac{i\text{corr, example pass.}}{i\text{corr, HNO}_3 \text{ pass.}}$$

A small ratio corresponds to a low corrosion current indicating the presence of a more protective passive film, as compared to the standard nitric acid passivation method. The less the polarization curves are affected by the initial surface conditions, the more effective the passivation method is for practical use.

The following examples do not limit the scope of the invention, but are intended to illustrate the effectiveness of the invention as described above and claimed hereafter.

EXAMPLE 1

A polished (mirror finish) stainless steel metallic coupon of AISI type 316L was wiped clean of debris and then thoroughly cleaned by typical cleaning methods, and thorough water rinsing.

A passivating solution of 25 grams per liter of Na$_2$SO$_4$.10H$_2$O (pH7) was prepared. The cleaned, metal coupon was then immersed in this solution, which was maintained at a temperature of approximately 22° C. for 16 hours to produce a spontaneous passive thin, uniform film on the coupon's surface.

EXAMPLE 2

A metallic coupon as described in Example 1 was cleaned according to Example 1 and then immersed in a passivating solution of 20 grams per liter of Na$_3$PO$_4$.12H$_2$O (pH4), which was maintained at a temperature of approximately 22° C. as for Ex. 1 for 16 hours, to produce a spontaneously passivated thin, uniform film on the surface of the coupon.

EXAMPLE 3

A polished (mirror finish) metallic coupon formed of cobalt-chromium-molybdemum was cleaned as described in Example 1. The coupon was then immersed in a passivating solution of 20 grams per liter Na$_3$PO$_4$.12H$_2$O to which had been added phosphoric acid to adjust the pH to pH4. The coupon was then maintained at a temperature of approximately 22° C. for 16 hours, to produce a spontaneously passivated thin, uniform film on the coupon's surface.

EXAMPLE 4

A metallic coupon as described in Example 3 was cleaned as described in Example 1. The coupon was then immersed in a passivating solution of 20 grams per liter Na$_3$PO$_4$.12H$_2$O (pH12), which was maintained at a temperature of approximately 22° C. for 16 hours, to produce a spontaneously passivated thin, uniform film on the coupon surface.

EXAMPLE 5

A metallic coupon as described in Example 1 was cleaned according to Example 1. The coupon was then immersed in a passivating solution of 25 grams per liter Na$_2$SO$_4$.10H$_2$O (pH7). The solution was heated to a temperature of 37° C., and the coupon was maintained in this heated solution for 24 hours, to produce a spontaneously passivated thin, uniform film on the coupon surface.

EXAMPLE 6

A metallic coupon as described in Example 3 was cleaned as described in Example 1. The coupon was then immersed in a passivating solution of 25 grams per liter Na$_2$SO$_4$.10 H$_2$O (pH7). The solution was heated to a temperature of 37° C., and the coupon was maintained in this solution for 24 hours to produce a spontaneously passivated thin, uniform film on the coupon surface.

EXAMPLE 7

A metallic coupon described in Example 1 was cleaned as described in Example 1. The coupon was then immersed in a passivating solution of 25 grams per liter Na$_2$SO$_4$.10H$_2$O (pH7) which was also aerated. A graphite rod, which was also immersed in this passivating solution, was mechanically coupled to the metallic coupon. The solution was heated to a temperature of 37° C., and the mechanically coupled coupon and graphite rod system were maintained in the solution for 24 hours. This mechanical contact established a natural galvanic couple with the resultant separation of the anode and cathode processes to produce a thin, uniform passivated film on the coupon surface.

EXAMPLE 8

A metallic coupon as described in Example 3 was cleaned according to Example 1. The coupon was then immersed in a passivating solution of 25 grams per liter Na$_2$SO$_4$.10 H$_2$O (pH7), which was also aerated. A graphite rod, which was also immersed in this passivating solution, was mechanically coupled to the metallic coupon. The solution was heated to 37° C., and the mechanically coupled coupon and graphite rod system was maintained in this solution for 24 hours to produce a thin, uniform passivated film on the coupon surface.

EXAMPLE 9

A polished (mirror finish) metallic coupon of titanium-6 aluminum-4 vanadium was cleaned according to the procedure described in Example 1. The coupon was then mechanically coupled to a graphite rod, and subsequently immersed in a passivating solution of 25 grams per liter Na$_2$SO$_4$.10 H$_2$O (pH7), which was also aerated. The solution was heated to a temperature of 37° C., and the mechanically coupled coupon and graphite rod system were maintained in the solution for 24 hours to produce a thin, uniform passivated film on the coupon surface.

EXAMPLE 10

The ratios of the passive current density (icorr) compared to the icorr for nitric acid passivation for each metallic coupon and passivation method described in Example 1-9 are listed in the Table 1 below. The nitric acid passivation procedure was performed in 20 vol. % nitric acid at a temperature of about 22° C. for 30 minutes. The potentiodynamic curves were determined in Lactated Ringer's solution open to air one day after passivation.

TABLE 1

| Passive Current Density Comparison | |
|---|---|
| Example | icorr, example pass. icorr, HNO$_3$ pass. |
| 1 | 0.60 |
| 2 | 0.67 |
| 3 | 0.10 |
| 4 | 0.09 |
| 5 | 0.47 |
| 6 | 0.08 |
| 7 | 0.33 |
| 8 | 0.06 |
| 9 | 0.17 |

Table 1 reveals that the inventive method resulted in significantly improved performance characteristics as compared to nitric acid passivation, as indicated by the lower ratio values. Samples passivated by the inventive method exhibited significantly lower corrosion current densities (I) and less positive corrosion potentials (E). Furthermore, the samples passivated by the inventive method were also less sensitive to the initial (i.e. prior to passivation) surface conditions.

EXAMPLE 11

Figure 1B:
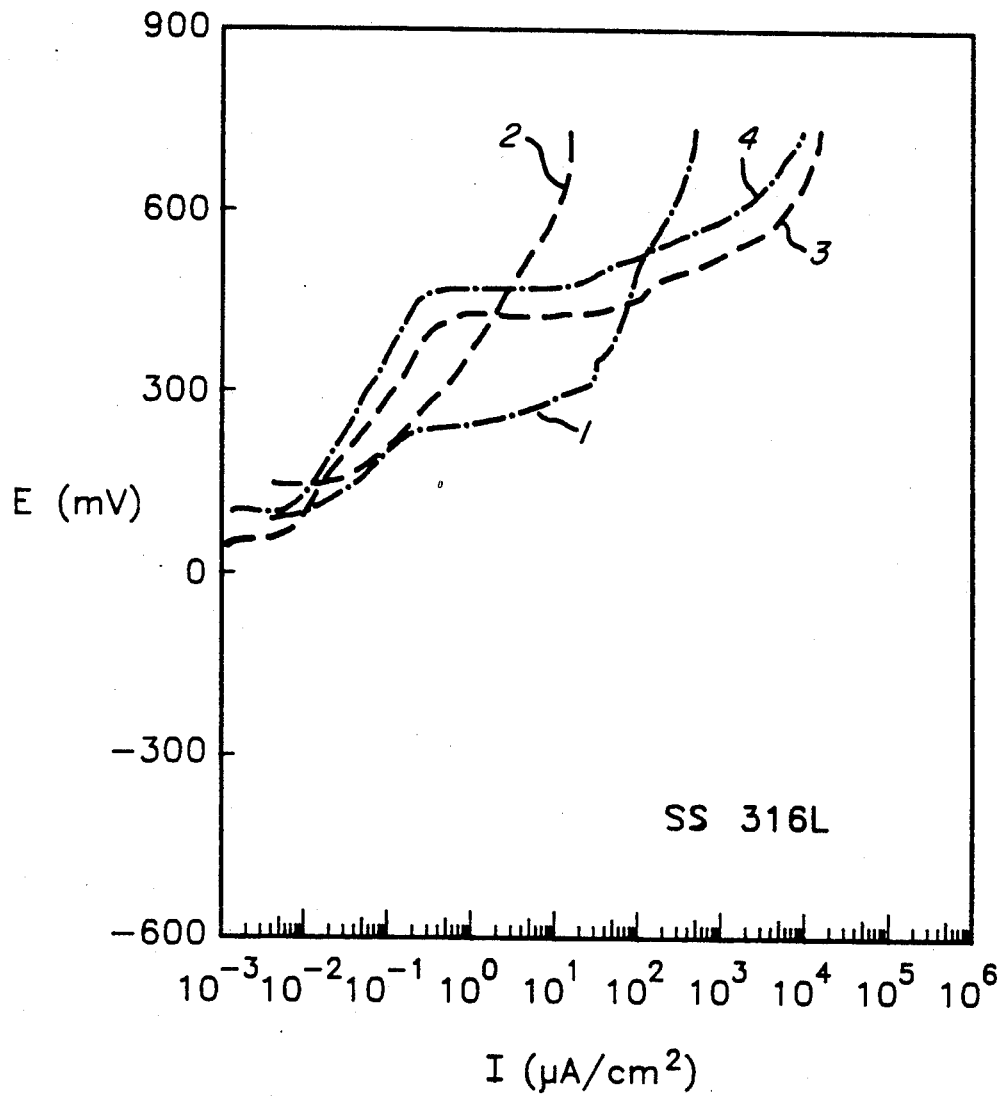

FIGS. 1a and 1b show potentiodynamic curves obtained for two 316L stainless steel coupons. Each coupon was used twice, once to test nitric acid passivation and then, after polishing, to test the inventive method of non-aggressive anion passivation. The passivation methods were as follows for each coupon:

Test 1: The coupon was polished and then passivated by immersing the coupon in a solution of 20 vol. % $HNO_3$ at a temperature of 23° C., for 30 minutes.

Test 2: The coupon was polished and then stored in air for a period of 24 hours prior to passivation. The coupon was then immersed in a passivating solution of 20 vol. % $HNO_3$, at a temperature of 50° C., for 20 minutes.

Test 3: The coupon used in test 1 was repolished and then passivated by galvanic coupling by immersing the coupon, coupled with a graphite rod, in an aerated passivating solution of 25 grams per liter 1672X$Na_2SO_4.10H_2O$ for a period of 24 hours.

Test 4: The coupon of test 2 was repolished and then stored in the air for a period of 24 hours prior to passivation via galvanic coupling as conducted for sample 3.

All of the above tests were conducted in a Lactated Ringer's solution conditioned at 37° C. for one hour. The potential was changed at a rate of 1 mV/sec.

EXAMPLE 12

Figure 2A:
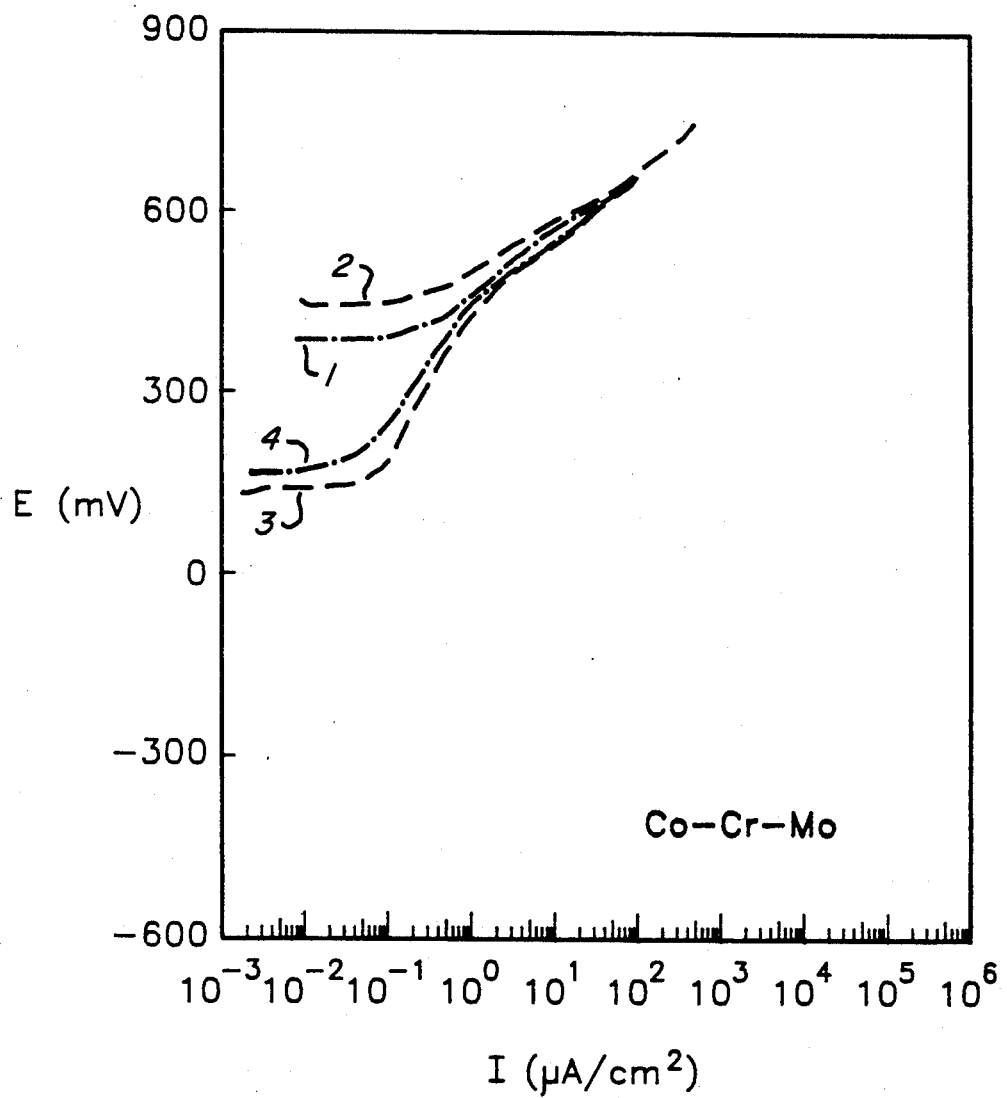
FIGS. 2a and 2b show the effect of initial and passivating conditions on two different samples of Cobalt-Chromium-Molybdenum alloy coupons.
Figure 2B:
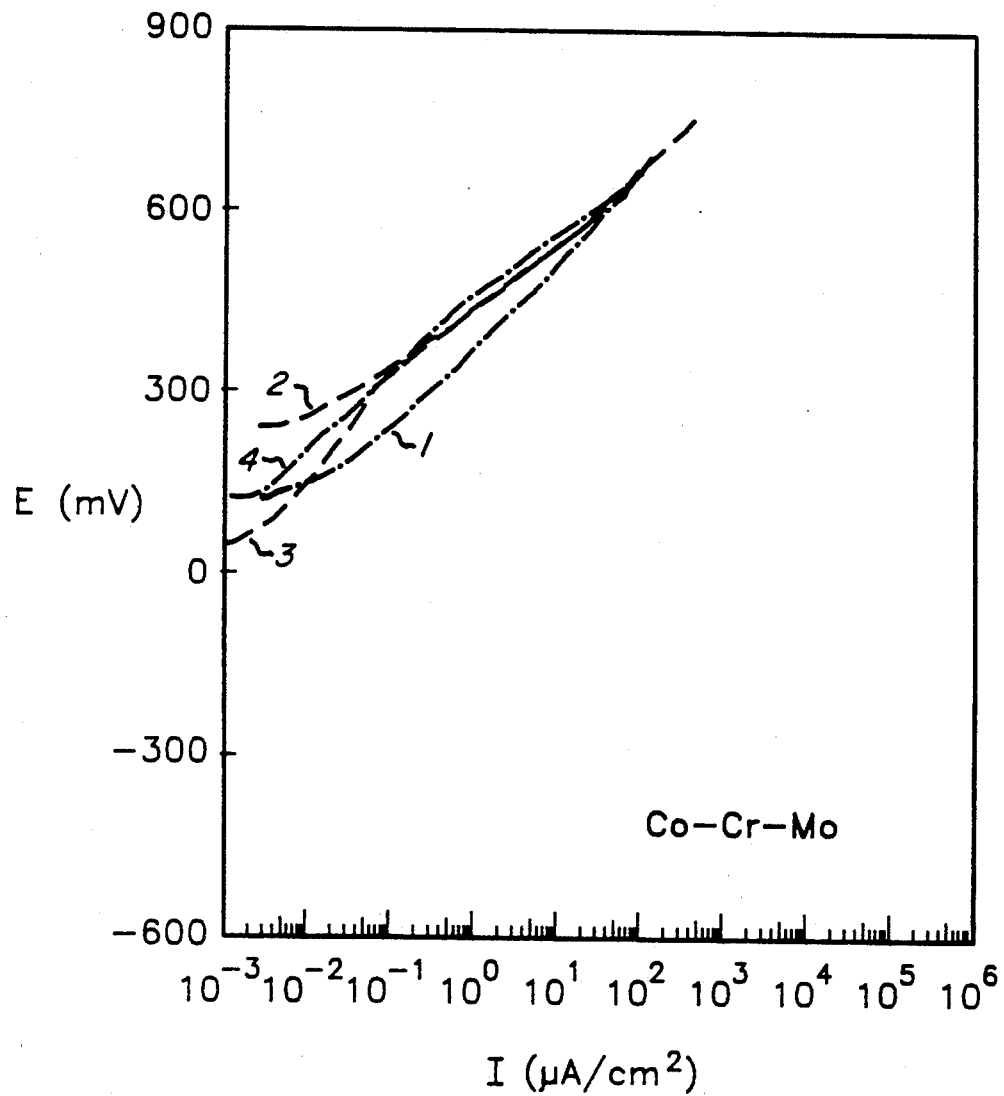

FIGS 2a and 2b show potentiodynamic curves obtained for two cobalt-chromium-molybdenum alloy coupons. Each coupon was used twice, once to test nitric acid passivation and then, after polishing, to test the inventive method of non-aggressive anion passivation. The passivation methods are as follows:

Test 1: The coupon was polished and then passivated by immersing the coupon in a passivating solution of 20 vol. % $HNO_3$, at a temperature of 23° C., for 30 minutes.

Test 2: The coupon was polished and stored in air for a 24-hour period prior to passivation. The coupon was then immersed in a passivting solution of 20 vol. % $HNO_3$, at a temperature of 50° C., for 20 minutes.

Test 3: The coupon used in Test 1 was repolished and then passivated by galvanic coupling by immersing the coupon, coupled with a graphite rod, in an aerated passivating solution of 25 grams per liter $Na_2SO_4.10H_2O$ for a period of 24 hours.

Test 4: The coupon used in Test 2 was repolished and then stored in air for a period of 24 hours prior to galvanic coupling as conducted for Test 3.

All of the above tests were conducted in a Lactated Ringer's solution conditioned at 37° C. for one hour. The potential was changed at a rate of 1 mV/sec.

EXAMPLE 13

Figure 3A:
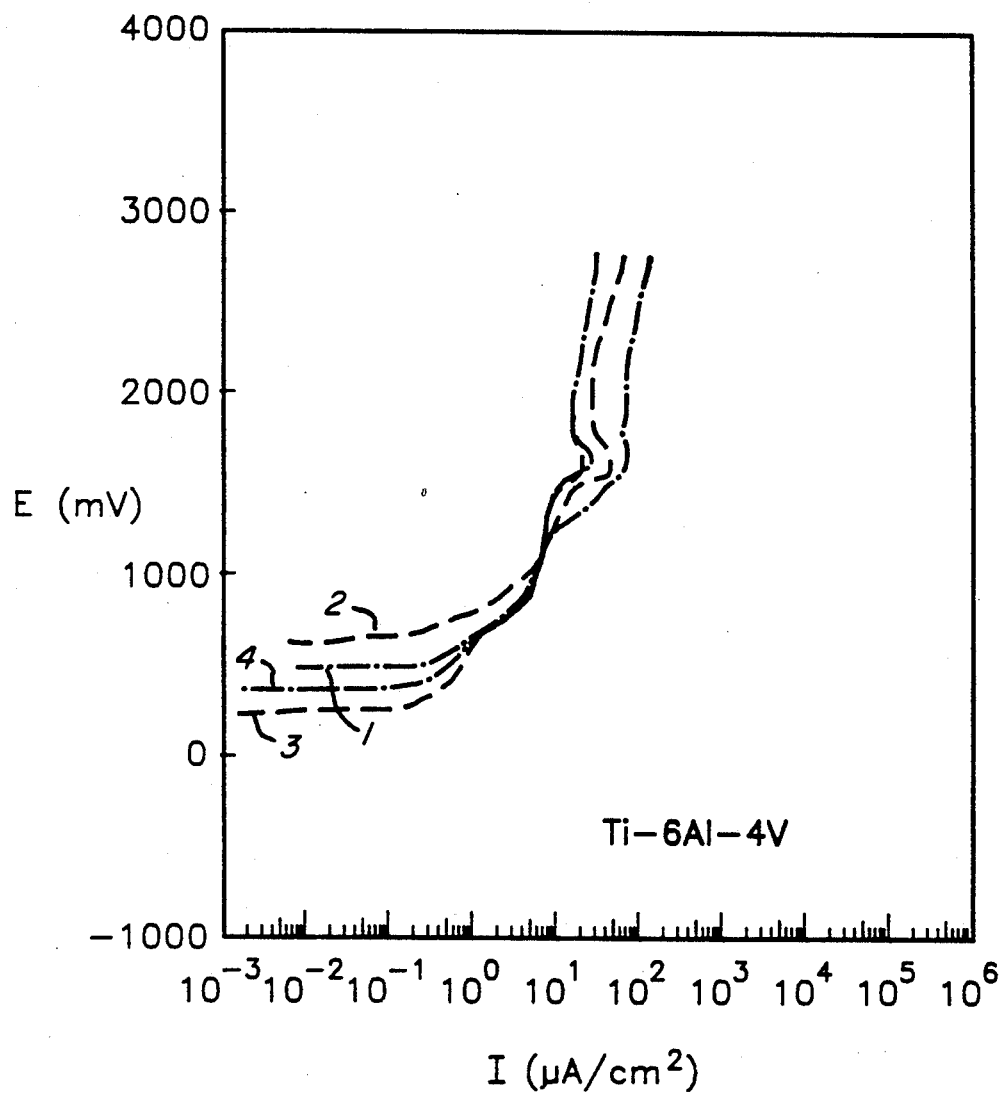
FIG. 3a and 3b show the effect of initial and passivating conditions on two different samples of Titanium-6 Aluminum-4 Vanadium alloy coupons.
Figure 3B:
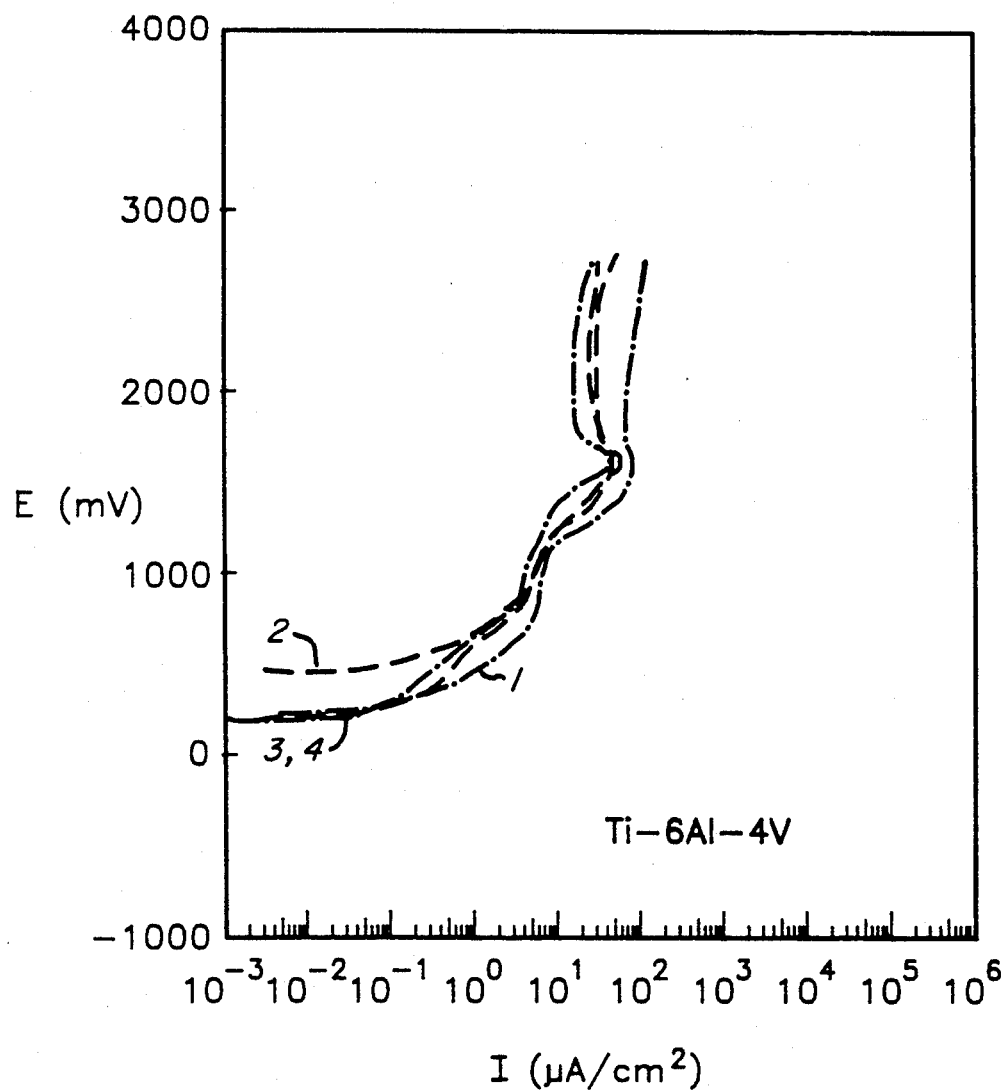

FIGS. 3a and 3b show potentiodynamic curves obtained for two Titanium-6 Aluminum-4 Vanadium alloy coupons. Each coupon was used twice, once to test nitric acid passivation and then, after polishing, to test the inventive method of non-aggressive anion passivation. The passivation methods are as follows:

Test 1: The coupon was polished and then passivated by immersing the coupon in a solution of 20 vol. % $HNO_3$ at a temperature of 23° C., for 30 minutes.

Test 2: The coupon was polished and then stored in air for a period of 24 hours prior to passivation. The coupon was then immersed in a passivating solution of 20 vol. % $HNO_3$, at a temperature of 50° C., for 20 minutes.

Test 3: The coupon used in test 1 was repolished and then passivated by galvanic coupling by immersing the coupon, coupled with a graphite rod, in an aerated passivating solution of 25 grams per liter $Na_2SO_4.10H_2O$ for a period of 24 hours.

Test 4: The coupon of test 2 was repolished and then stored in air for a period of 24 hours prior to passivation via galvanic coupling as conducted for sample 3.

All of the above tests were conducted in Lactated Ringer's solution conditioned at 37° C. for one hour. The potential was change at a rate of 1 mV/sec.

The invention has been described with reference to its preferred embodiments. A person of ordinary skill in the art, having read the above specification, may appreciate modifications that are within the scope of the invention as described above and claimed here below.

We claim:

1. A metallic medical implant having a surface covered at least partially with a thin surface film selected from the group consisting of metal oxides and hydroxides wherein the film is produced by the process comprising:
   a. immersing the metallic implant in a passivating solution, said solution comprising an aqueous solution of a water soluble metal salt containing an oxyanion in a concentration of from about 0.05 to about 0.25 equivalents per liter; and
   b. maintaining the passivating solution containing the implant to a temperature of from about 20° C. to about 50° C. for a time sufficient to form a thin, uniform tightly adherent coating of less than about 20 nanometers thickness.

2. The implant according to claim 1 wherein the metallic implant is fabricated from a material selected from the group consisting of titanium, zirconium, hafnium, vanadium, niobium, tantalum and their alloys.

3. The implant according to claim 1 wherein the metal ion of the water soluble metal salt is selected from the group consisting of the alkali metal ions.

4. The implant according to claim 1 wherein the oxyanion is selected from the group consisting of the sulfate, phosphate, monohydrogen phosphate, dihydrogen phosphate, and borate oxyanions.

5. The metallic implant of claim 1 wherein
   a. the step of immersing comprises immersing in an about 0.15 equivalents per liter aqueous solution of sodium sulfate; and
   b. the step of maintaining the passivating solution containing the implant comprises maintaining the passivating slution to a temperature of about 37° C. for about 24 hours.

6. The implant of claim 1 wherein the metallic implant is fabricated from a material selected from the group consisting of 316L stainless steel, cobalt-chromemolybdenum steel and Ti—6Al—4V alloy.

7. The implant of claim 1 wherein the metallic implant is fabricated from a metal alloy selected from the stainless steels.

8. A metallic medical implant having a surface covered at least partially with a thin surface film selected from the group consisting of metal oxides and hydroxides wherein the thin film is produced by the process comprising:
   a. mechanically coupling the implant to a cathode rod;
   b. immersing the metallic implant mechanically coupled to a cathode rod in a passivating solution, the solution comprising an aqueous solution of a water soluble metal salt containing a non-aggressive oxyanion in a concentration of from about 0.05 equivalents per liter to about 0.25 equivalents per liter; and c. maintaining the passivating solution containing the metallic implant and cathode rod at a temperature of from about 20° C. to about 50° C. for a time sufficient to form a passive uniform tightly adherent coating of up to about 20 nanometers thickness on the implant surface.

9. The implant according to claim 8 wherein the metallic implant is fabricated from a material selected from the group consisting of titanium, zirconium, hafnium, vanadium, niobium, tantalum and their alloys.

10. The implant according to claim 8 wherein the water soluble metal is selected from the group consisting of the alkali metals.

11. The implant according to claim 8 wherein the oxyanion is selected from the group consisting of the sulfate, phosphate, monohydrogen phosphate, dihydrogen phosphate, and borate oxyanions.

12. The metallic implant according to claim 8 wherein a. the step of immersing comprises immersing the mechanically coupled cathode rod and metallic implant in an about 0.15 equivalents per liter aqueous solution of sodium sulfate; and b. the step of maintaining the passivating solution comprises heating to a temperature of about 37° C. for about 16 hours.

13. The implant of claim 8 wherein the metallic implant is fabricated from a material selected from the group consisting of 316L stainless steel, cobalt-chrome-molybdenum steel and Ti—6Al—4V alloy.

14. The implant of claim 8 wherein the metallic implant is fabricated from a metal alloy selected from the stainless steels.

* * * * *